(12) United States Patent
Stonig (10) Patent No.: US 9,895,822 B2
(45) Date of Patent: Feb. 20, 2018

(54) AUTOMATED FRANGIBLE CANNULA BREAKER

(71) Applicant: Fenwal, Inc., Lake Zurich, IL (US)

(72) Inventor: Christian Stonig, Ernstbrunn N (AT)

(73) Assignee: Fenwal, Inc., Lake Zurich, IL (US)

( * ) Notice: Subject to any disclaimer, the term of this patent is extended or adjusted under 35 U.S.C. 154(b) by 239 days.

(21) Appl. No.: 13/833,990

(22) Filed: Mar. 15, 2013

(65) Prior Publication Data

US 2014/0263529 A1  Sep. 18, 2014

(51) Int. Cl.
*B26F 3/00* (2006.01)
*A61M 39/22* (2006.01)
*A61M 1/02* (2006.01)
*A61J 1/10* (2006.01)
*A61J 1/14* (2006.01)

(52) U.S. Cl.
CPC .............. *B26F 3/00* (2013.01); *A61M 39/221* (2013.01); *A61J 1/10* (2013.01); *A61J 1/1475* (2013.01); *A61M 1/02* (2013.01); *A61M 2039/222* (2013.01); *Y10T 225/371* (2015.04)

(58) Field of Classification Search
CPC ......... B26F 3/00; B26F 3/002; Y10T 225/30; Y10T 225/307; Y10T 225/321; Y10T 225/325; Y10T 225/364; Y10T 225/371; Y10T 225/329; A61M 39/221; A61M 2039/222; A61M 1/02; A61J 1/1475; A61J 1/10
USPC .............. 225/93, 94, 96, 96.5, 97, 102, 103
See application file for complete search history.

(56) References Cited

U.S. PATENT DOCUMENTS

| | | |
|---|---|---|
| 2,659,253 A | 12/1949 | Myrick |
| 3,266,287 A | 8/1966 | Gill |
| 4,181,140 A | 1/1980 | Bayham et al. |
| 4,294,247 A | 10/1981 | Carter et al. |
| 4,340,049 A | 7/1982 | Munsch |
| 4,386,622 A | 6/1983 | Munsch |
| 4,510,825 A * | 4/1985 | Neron ............... B25B 13/467 81/57.29 |
| 4,586,928 A | 5/1986 | Barnes et al. |
| 5,427,145 A | 6/1995 | Grabenkort |
| 5,709,685 A * | 1/1998 | Dombrowski ..... A61B 17/7037 24/336 |
| 5,824,216 A | 10/1998 | Joie et al. |

(Continued)

FOREIGN PATENT DOCUMENTS

WO  WO 1999/44652   9/1999
WO  WO 2004/058046 A2  7/2004

(Continued)

OTHER PUBLICATIONS

You Tube video—https://www.youtube.com/watch?v=7u677isN1Og, published on Jul. 26, 2012. (DVD enclosed).

(Continued)

*Primary Examiner* — Phong Nguyen
(74) *Attorney, Agent, or Firm* — Cook Alex Ltd.

(57) ABSTRACT

Apparatus and method are disclosed for opening a frangible internal cannula located in flexible fluid flow path. The frangible cannula has first and second portions joined by a frangible junction and the apparatus and method cause bending of one portion of the cannula relative to the other portion that results in breaking of the frangible junction and opening of the flow path to fluid flow therethrough.

22 Claims, 7 Drawing Sheets

(56) References Cited

U.S. PATENT DOCUMENTS

| | | | |
|---|---|---|---|
| 6,132,413 A | 10/2000 | Mathias et al. | |
| 6,156,025 A | 12/2000 | Niedospial, Jr. et al. | |
| 6,409,032 B1 | 6/2002 | Bekkers et al. | |
| 6,427,893 B1* | 8/2002 | Penrod | B29C 45/382 |
| | | | 225/103 |
| 6,470,780 B1* | 10/2002 | Benuzzi | 83/733 |
| 9,192,756 B2* | 11/2015 | Deverre | A61M 39/221 |
| 2001/0039404 A1 | 11/2001 | Rolle | |
| 2003/0167893 A1* | 9/2003 | Morris et al. | 83/649 |
| 2009/0227961 A1 | 9/2009 | Fresenius | |
| 2010/0132512 A1 | 6/2010 | Bucciaglia et al. | |
| 2010/0269584 A1* | 10/2010 | Horst | G01F 23/02 |
| | | | 73/293 |
| 2011/0198350 A1 | 8/2011 | Fresenius | |
| 2013/0340836 A1* | 12/2013 | Wambold | G05D 7/0617 |
| | | | 137/10 |

FOREIGN PATENT DOCUMENTS

| | | |
|---|---|---|
| WO | WO 2010/065396 A1 | 6/2010 |
| WO | WO 2012/080664 A2 | 6/2012 |
| WO | WO 2012/177158 A1 | 12/2012 |
| WO | WO 2014/083412 | 6/2014 |

OTHER PUBLICATIONS

European Search Report dated Mar. 4, 2014, for Application No. EP 13192157.9.

\* cited by examiner

AUTOMATED FRANGIBLE CANNULA BREAKER

The subject matter of this application relates to devices and methods for opening frangible closures or valves within fluid passageways, such as within fluid flow paths associated with blood collection or processing flow circuits or systems.

It is well known in the medical field and particularly in the blood banking field to employ frangible internal flow control valves in pre-assembled and pre-sterilized fluid flow circuits that are used in the collection and/or processing of human or animal blood or blood components, including without limitation umbilical cord blood (hereinafter "blood"). Such valves are commonly referred to as frangible or breakable valves, closures or cannulas and will referred to as cannulas herein. Numerous patents disclose various configurations of such frangible cannulas. See, for example, U.S. Pat. Nos. 4,181,140; 4,294,247; 4,340,049; 4,386,622 and 6,132,413, all of which are hereby incorporated by reference.

Such frangible cannulas may be located at any suitable location in a fluid flow system, such as within flexible fluid flow tubing for controlling flow through the tubing or within flexible port tubes associated with liquid filled or liquid-receiving containers to control flow into or from the container. Although the particular design can vary, typically such cannulas have two portions separated by a breakable zone or junction formed by an area of reduced or limited thickness. The user can open the cannulas by external manipulation without disturbing the internal sterility of the fluid flow path. For example, by gripping the flexible tubing or port tube and bending or flexing the cannula portions about the breakable junction, the junction can be broken and the portions separated to open the flow path. Although such is routinely done manually, it has been proposed to provide automated frangible cannula breakers, which breakers may be embodied in devices for processing pharmaceutical or biological fluids such as blood.

SUMMARY

The present subject matter is directed to apparatus and method for opening such frangible cannulas.

In one aspect or implementation of the present subject matter, apparatus is provided for breaking a frangible cannula located inside a flexible flow path. The frangible cannula is of the type including first and second portions with a breakable junction therebetween, which junction may be broken by relative bending of the portions. The breaking apparatus includes a first station in which the portion of the flow path containing the first portion of the frangible cannula is positionable and a second station in which the portion of the flow path containing the second portion of the cannula is positionable. The first and/or second station is movable relative to the other station to bend the flow path and the portion of the cannula therein relative to the other portion of the cannula to break the breakable junction and preferably further separate the portions to open the flow path to flow therethrough.

In another aspect or implementation of the present subject matter, which may be used with the above aspect or implementation, the first and/or second station is movable to bend the portion of the cannula therein in one direction relative to the other portion and in a direction opposite to the one direction.

In another aspect or implementation of the present subject matter, which may be used with any one of the above aspects or implementations, the first and/or second station is configured to repeatedly bend the portion therein in opposite directions.

In another aspect or implementation of the present subject matter, which may be used with any one of the above aspects or implementations, the first and/or second station comprises first spaced apart surfaces for receiving the flow path and a portion of the frangible cannula therebetween.

In another aspect or implementation of the present subject matter, which may be used with the above aspect or implementation, the spaced apart surfaces of one of the stations comprise fixed projecting members for receiving the flow path and a portion of the frangible cannula between the members.

In another aspect or implementation of the present subject matter, which may be used with any one of the above aspects or implementations, the first and/or second station is configured for movement through an arc relative to a center of rotation.

In another aspect or implementation of the present subject matter, which may be used with any one of the above aspects or implementations, the each station includes spaced apart surfaces for receiving the flow path and a portion of the cannula therebetween.

In another aspect or implementation of the present subject matter, which may be used with any one of the above aspects or implementations, the spaced apart surfaces of the first and/or second stations are off-set relative to a center of the arc of movement of one or both of the stations.

In another aspect or implementation of the present subject matter, which may be used with any one of the above aspects or implementations, the first and/or second stations are located so that when the frangible cannula is received therein, the breakable portion of the frangible cannula is generally axially aligned with or in proximity to the center of an arc of movement of such station or stations.

In another aspect or implementation of the present subject matter, which may be used with the apparatus employed for breaking a frangible cannula controlling flow through a port of fluid-containing bag, the apparatus includes a bag support for suspending the bag therefrom. The bag support is located relative to the first and second stations such that when a bag is suspended on the support, the first and second portions of the frangible cannula are located in proximity with the first and second stations for ease of insertion or positioning therein.

In another aspect or implementation of the present subject matter, which may be used with any one of the above aspects or implementations, the first and/or second station may be mounted on a rotary actuator.

In another aspect or implementation of the present subject matter, which may be used with any one of the above aspects or implementations, the first and/or second station is operable to bend the second portion through a bending arc in opposite directions relative to an initial loading position to break the cannula and move the portions further apart to open the flow path to fluid flow.

In another aspect or implementation of the present subject matter, which may be used with any one of the above aspects or implementations, a detector is provided for detecting when the frangible cannula is broken.

In another aspect or implementation of the present subject matter, which may be used with any one of the above aspects or implementations, the first and/or second station comprises a generally U-shaped recess or saddle for receiving the flow path and a portion of the frangible cannula.

In accordance with another aspect or implementation of the present subject matter, a method for breaking a frangible cannula located within a flexible flow path comprises mounting the flow path in a cannula breaker device having a first station for receiving a first portion of the cannula and a movable second station for receiving a second portion of the cannula, the frangible cannula having a breakable junction between the first and second portions, and actuating the first and/or second station to cause movement of the one station relative to the other station to break the breakable junction.

In accordance with another aspect, which may be used with the above aspect, the breaker device includes a detector for detecting whether the frangible cannula is broken, and the method includes detecting whether the cannula is broken.

In accordance with another aspect which may be used with any one of the above aspects, the first or second station may be in a fixed or stationary position.

BRIEF DESCRIPTION OF DRAWINGS

These and other aspects of the present subject matter are shown for purposes of illustration and not limitation in the attached drawings, of which.

DETAIL DESCRIPTION

Figure 1:
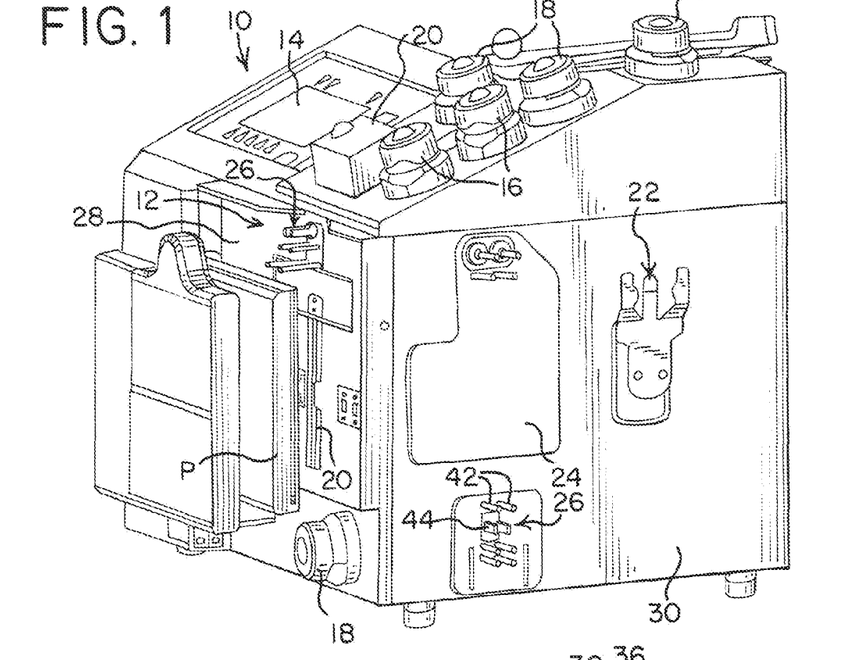
FIG. 1 is a perspective view of blood processing device or apparatus embodying a frangible cannula breaking device and method in accordance with the present subject matter.

Turning now to a more detail description, FIG. 1 illustrates durable or reusable fluid processing apparatus and more specifically a blood processing device or apparatus 10 for processing a container of blood previously collected from a source such as a human donor or patient, animal (e.g., equine blood), umbilical cord blood, etc.

In the present embodiment, the illustrated durable processing apparatus 10 is intended to cooperate with a disposable fluid flow or blood processing flow circuit that may include, for example, a primary blood bag or pouch, one or more satellite containers that can be empty or contain a nutritional or other fluid, and associated flow tubing filters and flow control devices, including one or more frangible cannulas. The apparatus 10 controls the flow of fluids through the fluid circuit to carry out one or more desired processes such as expression of plasma and/or red cells from a primary container and into a satellite container in combination with, if desired, a preservative. To that end, the apparatus 10 may include a front loading station 12 where a bag or pouch of blood can be suspended, a user interface 14 for receiving user commands and/or providing information, assorted valves 16, tube sealers/valves 18 and detectors 20, hangers 22 for filters and other hangers for additional bags or pouches, and one or more scales 24 for weighing containers, such as plasma, whole blood and other containers, and such additional features as may be desired.

In accordance with the present subject matter the apparatus preferably includes as least one apparatus 26 for breaking and opening a frangible flow control cannula in the fluid flow circuit. As illustrated, the processing apparatus 10 includes two frangible cannula breaking devices 26, one on the front panel 28 of the processing apparatus and one on the side panel 30.

Figure 2:
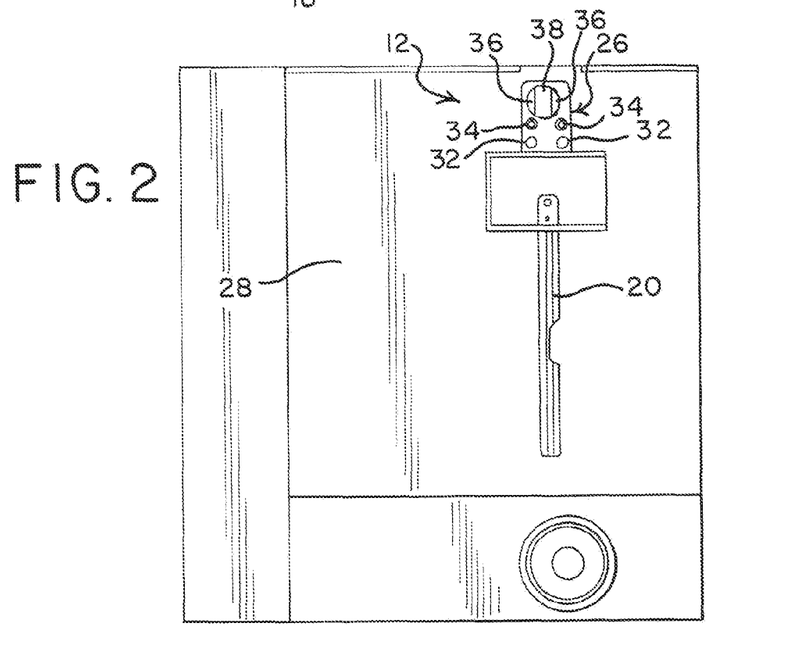
FIG. 2 is an elevation view of the front panel of the apparatus of FIG. 1, with portions removed for ease of viewing.
Figure 3:
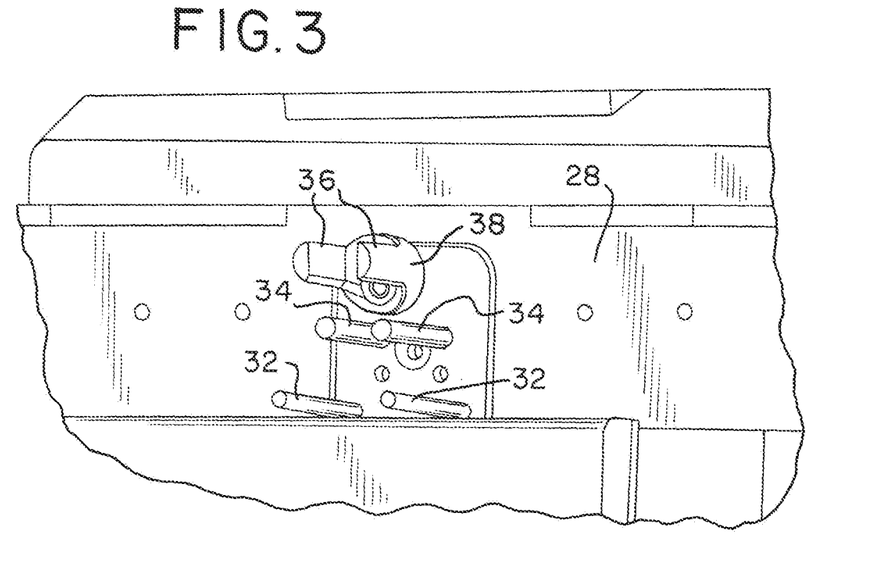
FIG. 3 is an isolated elevation view enlarged view illustrating the frangible cannula breaking apparatus of FIG. 1.

As seen in FIGS. 1-3, the front panel 28 includes a loading station 12 at which location a bag or pouch of collected blood may be suspended from mounting pins 32 that extend from the front panel. The pins may be attached to a scale or weighing apparatus for weighing the suspended bag. The pins may be exchangeable to fit bags from different manufacturers and may have tapered or pointed ends for penetration of bags not supplied with pre-arranged eyelets or slits for mounting.

The frangible cannula breaking apparatus 26 is situated above the bag mounting pins 32. As shown, on the front panel the cannula breaking apparatus has two loading or docking areas or stations into which the cannula is to be positioned, a first or lower station has spaced-apart surfaces, preferably spaced pins 34 (e.g., fixation pins) protruding from the front panel, and a second or upper station that has slot or groove between spaced surfaces formed by spaced fingers or wings 36 of a u-shaped channel or saddle 38. As illustrated, the pins 34 of the lower station are fixed relative to the front panel and to one another. The pins 34 are also preferably interchangeable, such as with the associated bag support pins 32, to accommodate bags of different manufacturers. Thus the first or lower station has a fixed position on the processing apparatus. The second or upper station is, in contrast to the first station, movable and preferably rotatable relative to the front panel and to the first station pins 34. Although described herein with reference to the relative positioning and movement shown, it should be understood that the relative position and movement may be reversed, with the first station rotatable and the second station fixed or both stations could be rotatable relative to one another. And the relative locations may also be reversed (effectively rotated 180 degrees), as may be required or beneficial for different containers/bags.

The fingers or wings 36 may be of any suitable shape or size and may be configured for the particular frangible cannula to be opened. For example, if a user typically employs the processing apparatus 10 with a fluid circuit or bags from a manufacturer or supplier that uses a frangible cannula of a particular design or material, the fingers or wings may be configured to cooperate most effectively with that particular frangible cannula. Compare, for example, the cross-sectional shapes of the fingers or wings 36 of FIG. 3 with those of FIG. 7. Specifically, the fingers or wings may be wider or narrower, have different cross-section shapes, such as round, oval, elliptical or rectangular, straight or curved sides, rounded corners or sharper corners and the like, such as may make the breaker more effective with a particular frangible cannula design or material. A selection of saddles could be available to allow the processing apparatus to be customized for use with a particular frangible cannula design or material or, alternatively, the processing apparatus 10 could be provided with a more universally applicable finger/wing shape and size that works with a wide variety of cannula designs or style or materials. This discussion also fully applies the size and shape of stationary pins 34. As discussed in more detail below, the apparatus 10 also could be programmable to vary the actual cannula breaking action depending on the particular cannula being broken.

Although the frangible cannula breaking apparatus 26 is situated above the bag mounting pins 32 on the front panel, as can be seen in FIG. 1, the frangible cannula breaker 26, on the side panel 30 is located below bag support or mounting pins 40 and the first and second stations formed by pins 42 and saddle 44 are inverted relative to the respective positions on the front panel 28. Additional cannula breaking apparatus can be provided on the apparatus at any suitable location and in any orientation for cooperation with the desired tubing or bag containing the frangible cannula to be broken, such as for use with containers from different manufacturers where a different orientation may be beneficial. Additional cannula breaking apparatus in accordance with the subject matter herein could also be provided on ancillary flow control apparatus used with the processing apparatus 10, or could be provided as a freestanding unit for use in a variety of settings not necessarily associated with the processing apparatus 10.

Figure 4:
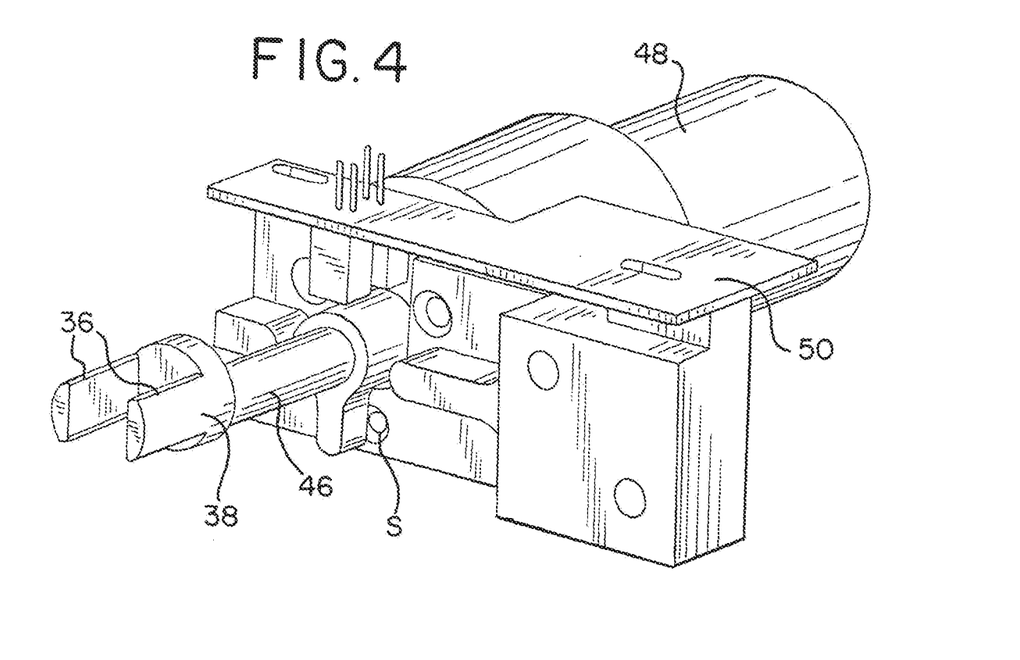
FIG. 4 is a perspective view of a movable portion of the frangible cannula breaking apparatus mounted on the shaft of a rotary drive motor.

FIG. 4 shows an isolated perspective view of the saddle 38, which defines the spaced apart surfaces of the second cannula docking/loading station on front panel 28. As shown there, saddle 38 is mounted on rotary shaft 46 connected to electrical motor, such as a DC drive motor or stepper motor 48, such as with a position encoder to allow monitoring of the rotational position of the motor. Support frame 50 mounts the motor 48 within the processing apparatus 10 behind front panel 28, and shaft 46 extends through the front panel to position the saddle as shown in FIGS. 1-3, above an in alignment with first station pins 34.

As best seen in FIG. 4, the saddle 38 is attached to motor-driven shaft 46. Spaced apart fingers or wings 36 extend from diametrically opposed positions on the base, forming u-shaped slot into which part of the frangible cannula is positioned or docked. The saddle 38 is mounted in an off-center relation to the shaft, with the center of saddle base being vertically offset from the center (or axis of rotation) of shaft 46. This off-center position has a benefit in breaking the cannula and encouraging separation of the cannula portions after breaking to better assure a fully open fluid flow path. The consequence of this positioning will be more evident from the discussion below.

Figure 5:
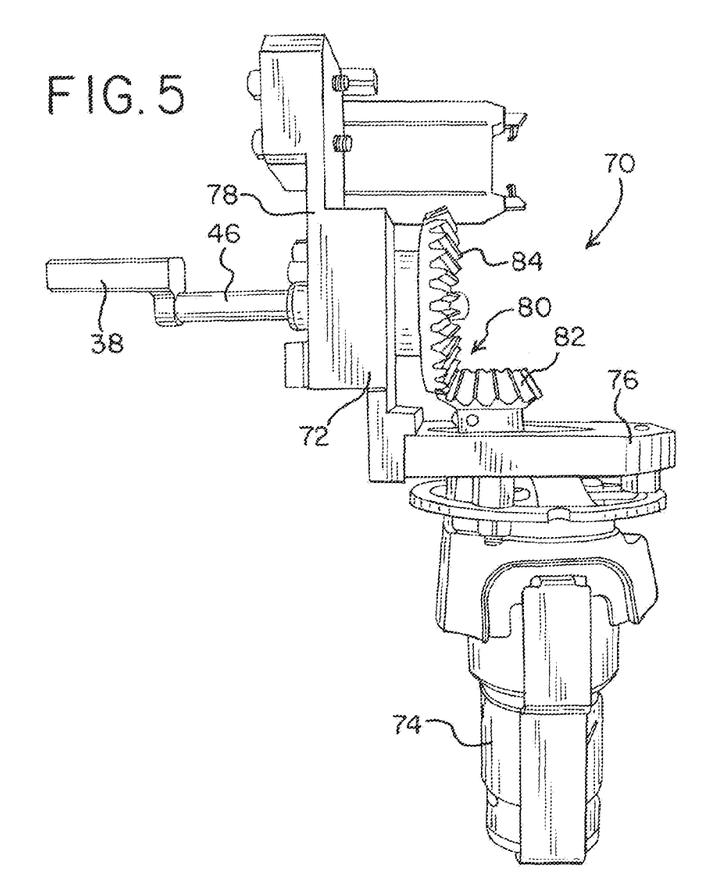
FIG. 5 is a perspective view of an alternative drive assembly for rotating the frangible cannula breaking apparatus.

FIG. 5 illustrates an alternative drive assembly, generally at 70 for rotating the saddle 38 of the cannula breaking apparatus with increased torque. This assembly may be used as needed instead of the direct drive assembly of FIG. 4, for any desired cannula breaker where extra torque is desired. This assembly includes a generally L-shaped mounting base 72 for mounting behind the front panel 28 of processing apparatus 10. A motor 74, such as an electric, e.g., stepper motor, is mounted to a horizontal leg 76 of the base 72. Saddle 38 is mounted on the end of rotary shaft 46, which is rotatably mounted in a vertical leg 78 of base 72 for extension through the front panel 28. For connecting the drive motor 74 to the shaft 46, the assembly includes a power transmission 80. The transmission may include gears, belts or pulleys, but is illustrated using a pair of beveled gears 82 and 84 rotationally mounted on the base 72. Bevel gear 82 is rotated directly or indirectly by drive motor 74 and bevel gear 84 is attached directly or indirectly to shaft 46. The bevel gears are engaged with one another so that rotation of the motor 74 and bevel gear 82 drives bevel gear 84 to rotate shaft 46. As seen in FIG. 5, gear 82 is of smaller diameter that gear 84. As a result, the rotation speed (RPM) of the larger bevel gear is slower than the rotational speed (RPM) of the smaller bevel gear, and the torque generated by the motor is amplified by the gear train so as to provide increased torque to shaft 46 to better assure sufficient torque for breaking the frangible cannula.

Figure 6:
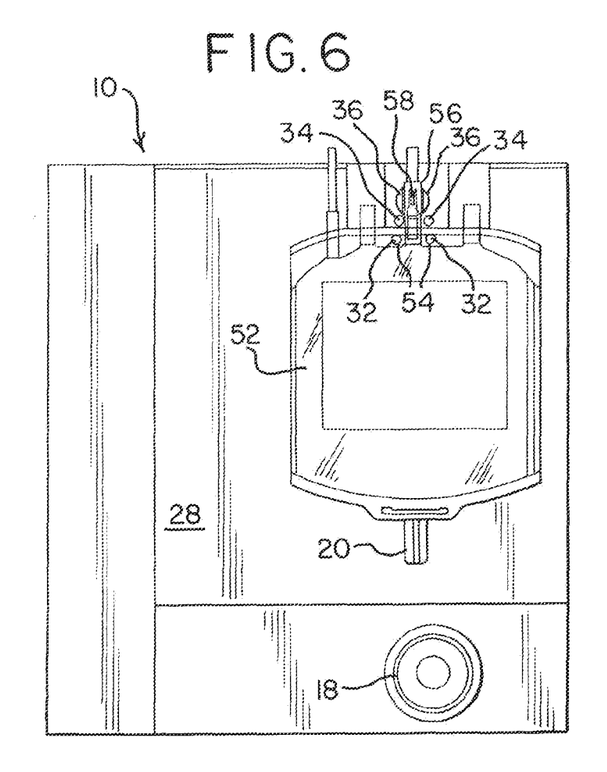
FIG. 6 is a partial front view of the apparatus of FIG. 2, which a fluid bag or pouch mounted in association with the frangible cannula breaking apparatus.

FIG. 6 shows the front panel 28 of processing apparatus 10, with a bag or pouch 52 mounted thereon and with certain portions of the processing apparatus removed for ease of viewing. More specifically, the bag or pouch 52 may contain a quantity of blood previously collected from a donor or patient. Typically, the blood bag will have previously been subjected to centrifugation to separate the blood cells based on density.

The bag 52 is suspended on the front panel 28 by inserting mounting pins 32 through matching eyelets 54 in the end perimeter of the bag. The particular processing apparatus 10, as seen in FIG. 1, includes a movable pressure plate P which can be automatically moved by the processing apparatus to contact and compress the bag 52 to express blood or blood components from the bag. The plate P and associated apparatus are removed in FIG. 5 for ease of viewing. As is common in blood bags, the bag includes a port tube 56 that communicates with the interior of the bag for flowing fluid into or from the bag. As illustrated, port tube 56 is sealed by an internal frangible cannula 58. The port tube 56, internal frangible cannula 58 and breaking apparatus 26 are shown in enlarged isolated detail in FIGS. 7-14, and reference should be made to those figures. The frangible cannula 58 shown in FIGS. 9-14 is but one example of frangible cannulas that may be opened using the present apparatus, and the present subject matter is not limited to the particular cannula design details shown. The frangible cannula 58, as with most such frangible cannulas in the medical fluid or blood processing fields, has first and second portions 60 and 62, preferably elongated and axially aligned, connected by a breakable junction 64 of relatively thin material. Typically made of rigid plastic, the frangible cannula is sealed within the port (or other flow tubing) and initially blocks fluid flow. Flexing of one portion of the cannula relative to the other portion causes the frangible junction to break and opens the lumen of the port tube to flow of fluid therethrough.

Figure 9:
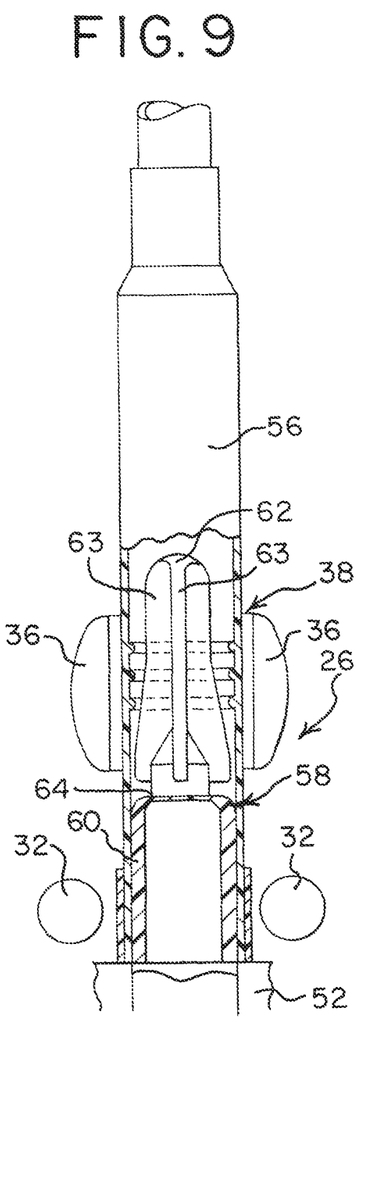
FIG. 9 is an enlarged isolated view of the present cannula breaking apparatus showing a container port tube and internal frangible cannula located in an initial loading position in the cannula breaking apparatus.

As best seen in FIG. 9, the first portion 60 of cannula 58 is in the form of a hollow tube, sealed at its upper end by the solid second portion 62 which has radially extending ribs or wings 63 to engage the inner surface of the tube when the cannula is broken while allowing fluid to flow past. Other manufacturers may use other structures, such as pins or other configurations to frictionally engage the inner surface of the port or other tube, and the present subject matter is not limited to a particular structure. The first portion 60 is fixedly attached within the port tube such as by solvent bonding, heat bonding or the like. The first and second portions are joined by a relatively thin web of plastic material that breaks reasonably easily when the portions are relatively flexed. Flexing of the second portion relative to the first and preferably axial separation of the second from the first opens the port tube to fluid flow. This particular frangible cannula is described in greater detail in prior U.S. Pat. No. 6,132,413, incorporated by reference herein, and is shown only for purposes of illustration. The present breaking apparatus is intended to work with frangible cannulas of various and differing specific designs.

Figure 7:
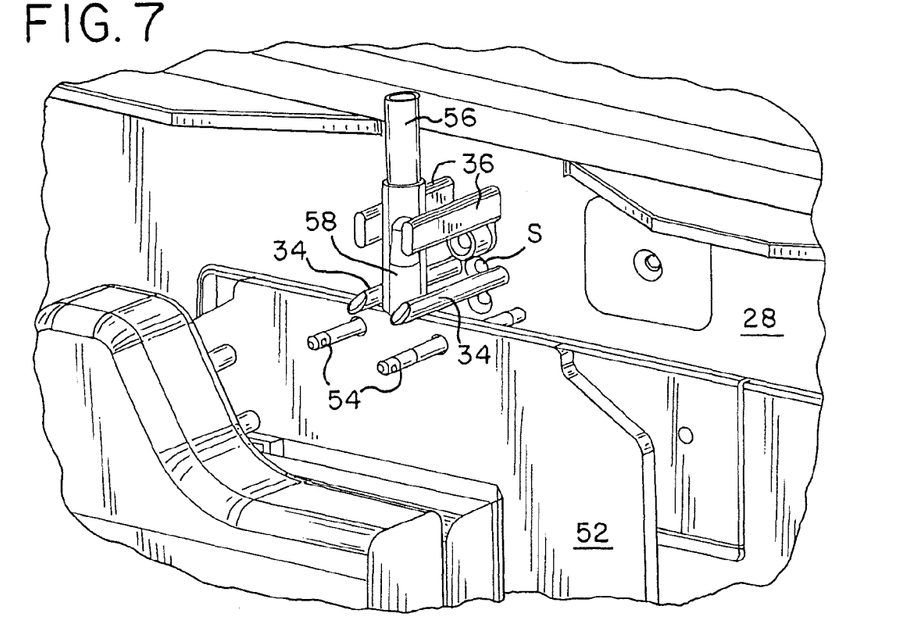
FIG. 7 is an enlarged isolated perspective view of the apparatus of FIG. 2, with a fluid bag or pouch mounted in association with the frangible cannula breaking apparatus.
Figure 8:
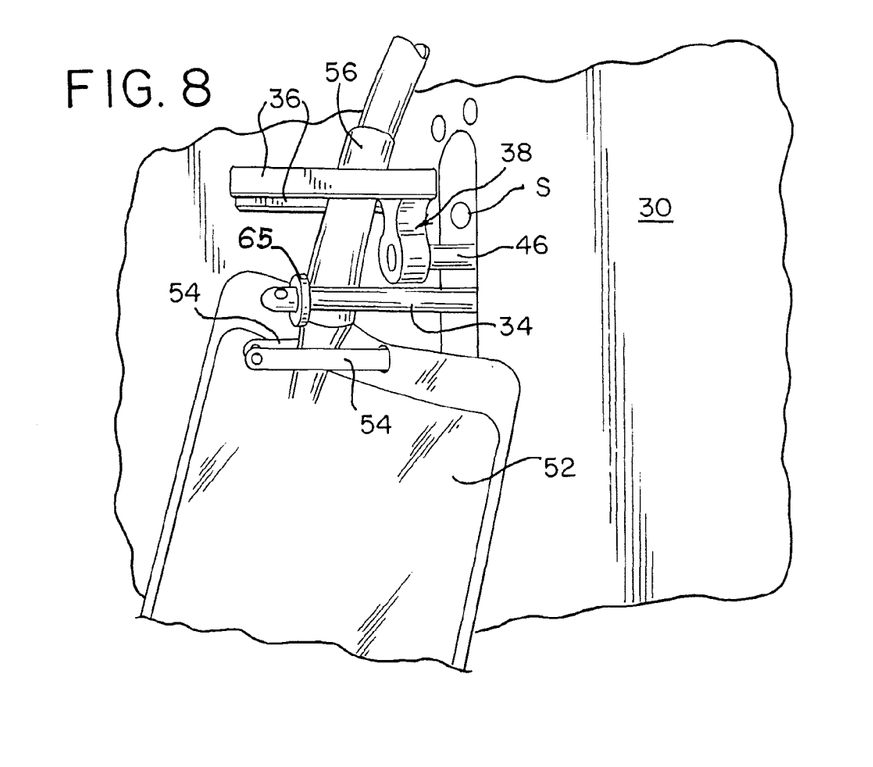
FIG. 8 is an enlarged isolated perspective view of the apparatus of FIG. 1, with a fluid bag or pouch mounted in association with the frangible cannula breaking apparatus located on the side of the processing apparatus.

Turning now to a more detailed discussion of the frangible cannula breaking apparatus and its method of use, as will be appreciated from FIGS. 6-8, when bag 52 is suspended, such as from mounting pins 32, the port tube 56 and frangible cannula 58 within the tube is conveniently mounted proximal to, and preferably in alignment with, the breaking apparatus 26. More specifically, when a bag is suspended on the front of apparatus 10, the port tube 56 and frangible cannula 58 are, by reason of the relative location between the bag support (mounting pins 32) and the pins 34 and saddle 38, located so as to be adjacent to and aligned with the breaking apparatus 26—with the first portion 60 of the frangible cannula 58 and the portion of the port tube in which it is located being positioned in or proximal to the first docking or loading station between pins 32 and the second portion 62 of the frangible cannula 58 and the portion of the port tube in which it is located being positioned in or proximal to the second docking or loading station between the spaced fingers 36 of saddle 38. The operator may then simply confirm proper positioning or, with relative ease, position the port tube and frangible cannula in proper association with the first and second cannula breaker stations. In this position, the frangible junction 64 of the cannula is located substantially in axial alignment with or in proximity to the axis of the rotary shaft 46, which promotes fracturing when the breaking apparatus is actuated. The processing apparatus preferably includes one, two or more sensors, such as an optical sensor "S" in the front panel, to detect the presence of the port tube in the proper position and enable further functioning of the breaker apparatus. Other types of sensors or detectors could also be used. Resilient rings 65 on pins 34 (see FIG. 8) assist in holding the port tube 56 between the pins 34 during the cannula breaking, and the port tube can be positioned between the rings 65 and the face of the processing apparatus 10 or the rings can be located between the port tube and the face of the apparatus if desired. Alternatively, in place of rings 65, a cylindrical shaft or block with an annular flange at one end could be used. This may find application more particularly with certain containers such as, for example, a whole blood pouch suspend on the side of the process apparatus.

Figure 10:
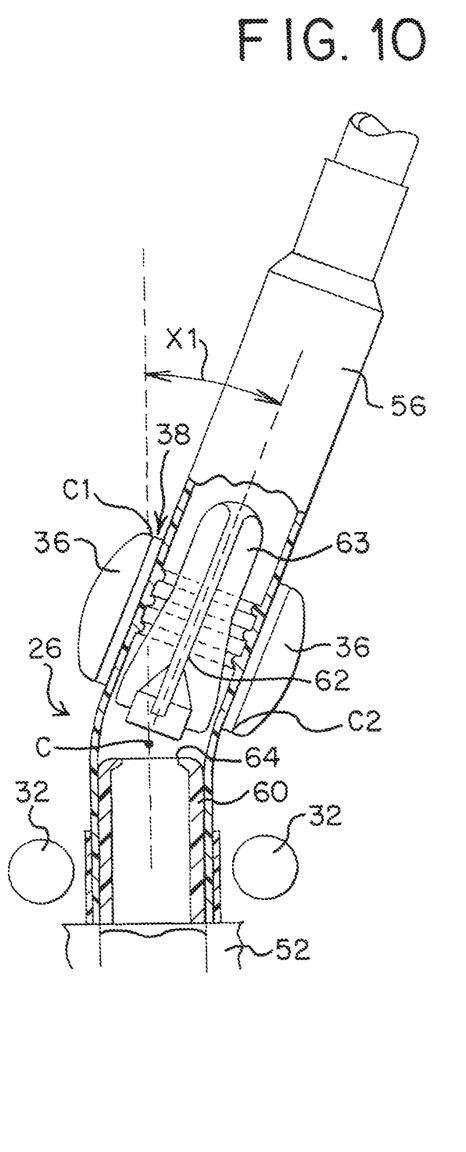
FIG. 10 is similar to FIG. 9, but illustrates the cannula breaking apparatus in a first position, bending a portion of the frangible cannula through a bending arc X1 relative to the other portion.

The actual breaking and opening of the frangible cannula preferably occurs automatically in response to a command from the operator or from the processing control system for the processing apparatus, and preferably only after the sensor S and control system determine that the frangible cannula port tube is properly located with the breaker apparatus. Referring to FIGS. 9 and 10, upon command, the motor 48 rotates or pivots the saddle 38 (and the second part of the frangible cannula) in one direction, such as clockwise about center of rotation C, through a selected angle X1 from a loading position (FIG. 9) to a first bent position (FIG. 10). In this embodiment, as noted earlier, the saddle 38 and fingers 36 are off-center relative to the axis of rotary shaft 46, and the frangible junction 64 is approximately in alignment with or in proximity to the axis of rotary shaft 46 and center of rotation C. Although such positioning may be beneficial, it is not required for all embodiments. Angle X1 may be any suitable amount of angle, and may extend either clockwise or counterclockwise, to fracture or begin to fracture the breakable junction 64 of cannula 58, and the amount and direction of rotation may be different for other cannula configurations or materials or suppliers. Angle X1 will typically be between 0 and 90 degrees and may be less than 60 degrees, such as 45 degrees or less, for example between about 15 and 40 degrees. While the second portion of the cannula is bent to angle X1 relative to the vertical axis, the first portion 60 of the frangible cannula 58 is held sufficiently vertical and stationary by fixed pins 34 to promote fracture of the breakable junction 64.

Figure 11:
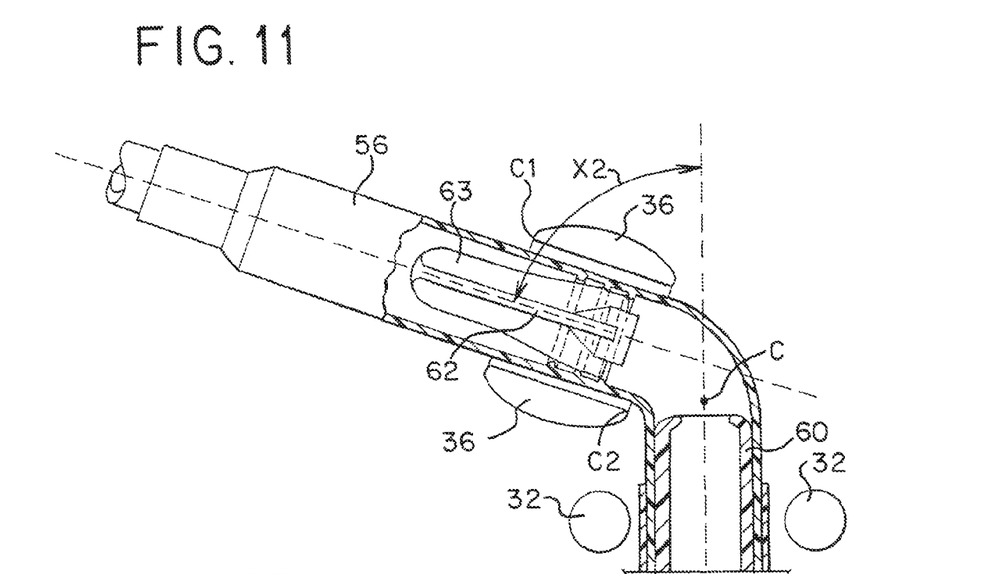
FIG. 11 is similar to FIG. 10 but illustrates the cannula breaking apparatus in a second position, bending a portion of the frangible cannula in the opposite direction through an opposite bending arc X2 greater than that in FIG. 10.
Figure 12:
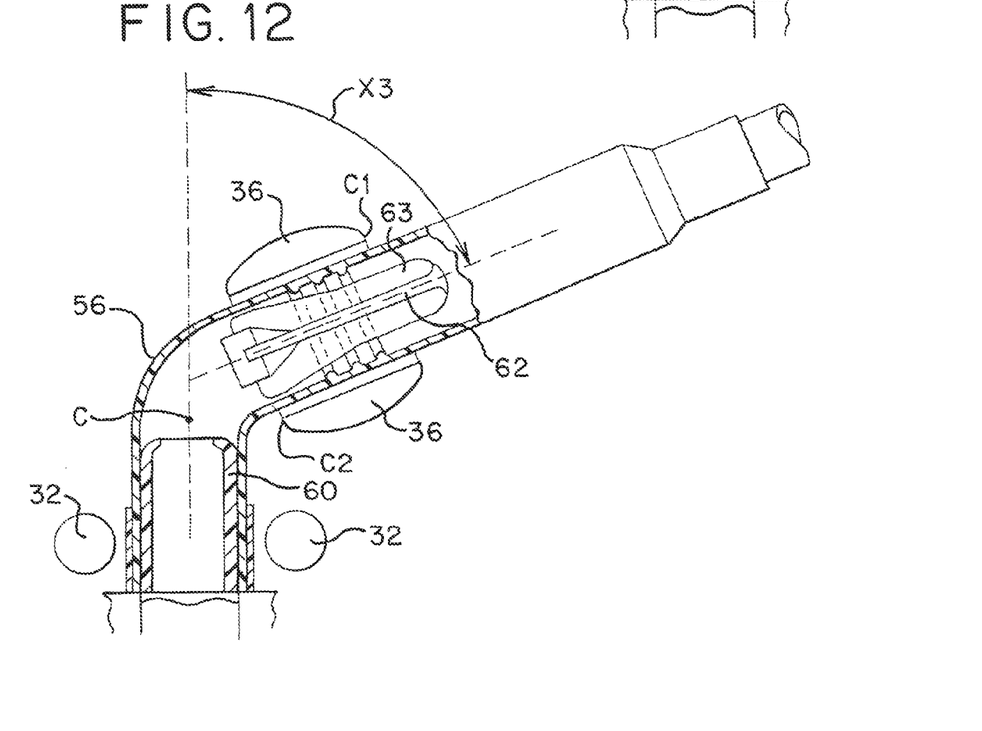
FIG. 12 is similar to FIG. 11 but illustrates the cannula breaking apparatus in a third position, bending a portion of the frangible cannula in the opposite direction of FIG. 11, and through a bending arc X3 approximately the same or greater than in FIG. 11.
Figure 13:
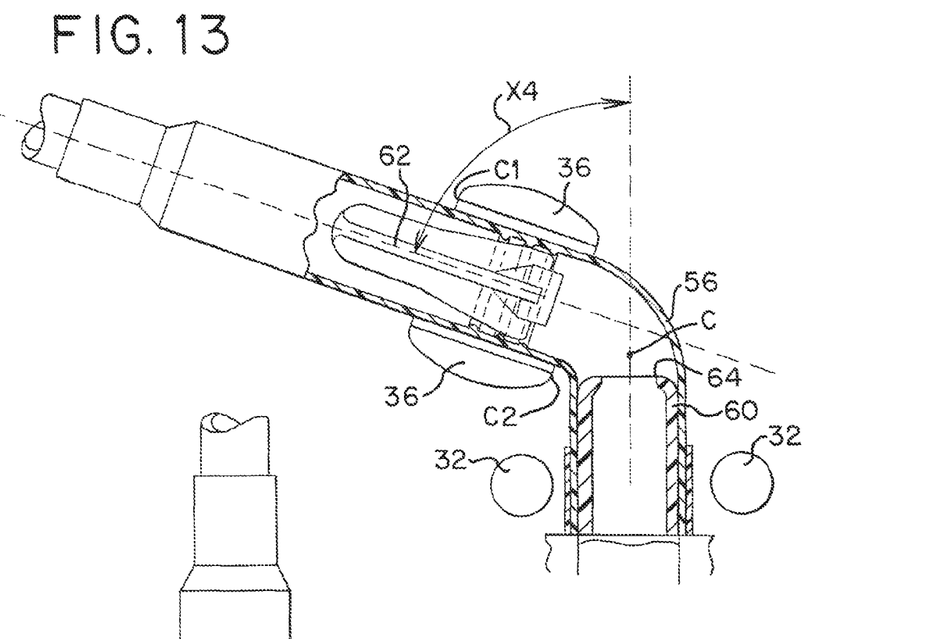
FIG. 13 is similar to FIG. 12 but illustrates the cannula breaking apparatus in a fourth position, bending a portion of the frangible cannula in the opposite direction of FIG. 12, and through a bending arc X4 approximately the same or greater than in FIG. 12.

After pivoting the saddle 38 and second cannula portion 62 in the first direction as seen in FIG. 10, the motor 48 reverses direction and pivots the saddle 44 and cannula portion 62 in the reverse direction, e.g. counterclockwise, preferably to a second position at an angle X2 about center C, as shown in FIG. 11, to further induce or cause fracture of the cannula 58. This angle X2 may be, for the particular cannula shown herein, preferably greater than the angle X1 in the first position and may be as much as 70-80 degrees. The motor then reverses again to rotate the cannula portion 62 to a third position with an angle X3 as shown in FIG. 12, which may be about equal to or greater than angle X2. A further rotation counterclockwise to angle X4 is shown in FIG. 13 and angle X4 may be about the same as or greater or lesser than X3.

Figure 14:
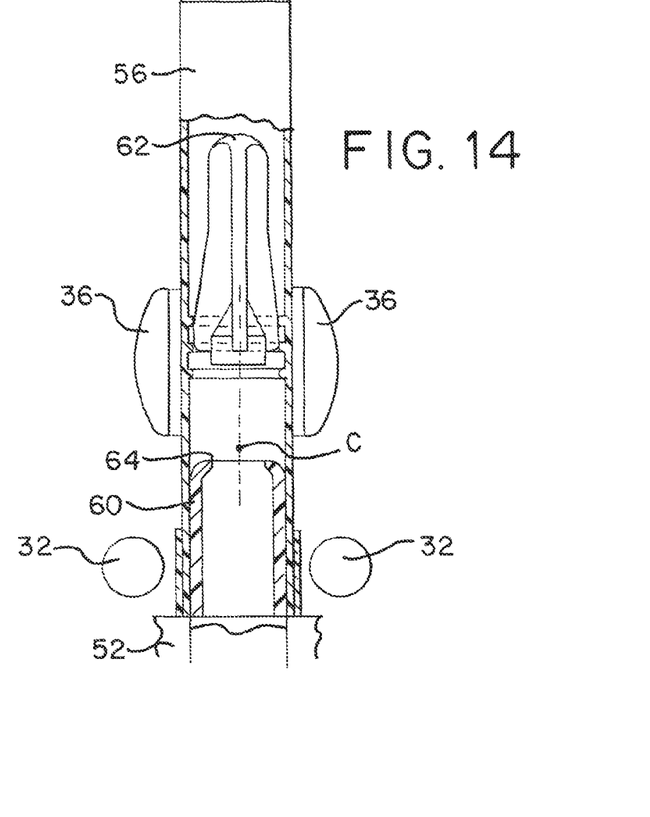
FIG. 14 illustrates the frangible cannula in the port tube of FIG. 9 after it has been broken and the port tube is open to fluid flow.

The motor may repeat this bending back and forth in opposite directions a fixed number of times, as is needed for the particular cannula being broken, returning the cannula eventually to the loading position, but in a fully open condition as shown in FIG. 14. For some cannula of highly rigid materials, one cycle back and forth may be enough to fully open the cannula. For cannulas of somewhat softer material, repeated cycles back and forth may be required. This may be predetermined and the processing apparatus configured for a particular cannula, as described below. Alternatively, the cannula may be flexed back and forth until an open flow path is detected by the processing apparatus, such as by detecting fluid flow through the port tube or a change in pressure in the bag 52, or by detecting a change in weight in one of the weight scales which is indicative that the cannula is open and fluid is flowing. FIG. 14 illustrates how the frangible cannula 58 may appear after repeated flexing of the cannula by the apparatus of the present disclosure, with the frangible or breakable junction 64 broken and portions 60 and 62 separated, thus opening the port tube for flow of blood or other liquid from or into the bag 52 without required manual manipulation by the operator or user.

It should be noted that FIGS. 9-14 illustrate the cannula breaker action diagrammatically for purposes of illustration and simplicity. When the fingers or wings 34 rotate, of course, they actually engage and press against the side of the port tube, and bend the cannula within the port tube. More specifically, with the fingers or wings 34 of the shape shown herein, which are preferably but not exclusively elongated in a vertical direction, opposite corners of the fingers will tend to engage the port tube when rotated. For example, referring to FIG. 11 of the panel of the processing apparatus, upper inside corner C1 of trailing finger 34 and lower inside corner C2 of the lead finger 34 will tend to engage most directly against and depress the wall of the port tube ("trailing" and "leading" are with reference to the direction of rotation). This action, when repeated, assists in breaking the cannula, particularly with the cannula is made of a somewhat softer or more pliable material, and also tends to push or "walk" the second cannula portion 62 axially along the inside of the port tube causing it to further separate from the first cannula portion after frangible portion or zone 64 is broken. For the particular cannula shown in the figures, the fingers or wings 34 may be pivoted back and forth several cycles, with increasing degrees of rotation up to about 70-80 degrees from vertical in both clockwise and counterclockwise directions. Other styles of frangible cannulas or cannulas made of more rigid materials may require only one or two cycles of the fingers to break and separate the cannula to allow flow through the port tube.

In this regard, the control system of the processing apparatus 10 may be programmable to vary the number of cycles and degree of rotation, depending on the frangible cannula to be broken. The control system may include a user selection feature, where the user selects from one or more frangible breaking protocols depending on the type or source of cannula to be broken, or the system may be configured to set the appropriate protocol upon reading a barcode or RFID tag associated with the particular bag or pouch. For those blood processing centers that tend to use disposable bags and blood collection and processing systems from a single source, with a single cannula configuration, the cannula breaking protocol may set at the factory or by service personnel and not routinely changed by the processing center.

As noted earlier, the illustrated apparatus also include one or more frangible cannula breakers on side panel 30 or elsewhere on the processing apparatus 10 or on ancillary equipment used in conjunction with the apparatus that functions substantially as described herein. On the side panel, the breaker is located to be employed with bags or pouches that are suspended in an inverted position relative to the bag 52. The cannula breaker functions essentially as described above, but with the relative parts inverted as compared to the front panel. Also, it is similarly positioned to be in proximity to the port tube and frangible cannula of the pouch or bag suspended on the side panel from the respective container mount.

Although the breaking apparatus 26 is described as used with a frangible cannula on the port tube of a container, it also has utility for opening frangible cannulas that are in fluid flow tubing not directly associated with a bag or container port. Also, the frangible cannula breaking apparatus, although shown in combination with a blood processing apparatus 10, may be freestanding and independent of any other associated processing device or apparatus.

While described in terms of the illustrated embodiments, it is understand that the features and implementations of the illustrated design may be varied in a manner apparent to those skilled in the field.

The invention claimed is:

1. Apparatus for breaking a frangible cannula located inside a flexible flow path, the frangible cannula including first and second portions with a breakable junction therebetween that may be broken by relative bending of the portions, the apparatus comprising: a stationary first station in which the portion of the flow path containing the first portion of the cannula is positionable and a pivotable second station in which the portion of the flow path containing the second portion of the cannula is positionable; an actuator connected to the pivotable second station and pivoting the second station from an initial loading position, in which the first and second stations are generally aligned, through one angle less than 90 degrees from the initial loading position in one direction and through a greater angle from the initial loading position in an opposite direction, the stationary first station being stationary relative to the initial loading position, wherein the second pivotable station is operable to bend the flow path and second portion of the cannula therein relative to the other portion of the flow path and the first portion of the cannula therein through a first angle in one direction and through a second greater angle in an opposite direction to break the breakable junction.

2. The apparatus of claim 1 in which the pivotable second station comprises spaced apart surfaces for receiving the flow path and a portion of the cannula therebetween.

3. The apparatus of claim 2 in which the spaced apart surfaces are off-set relative to a center of an arc of movement.

4. The apparatus of claim 2 in which the spaced apart surfaces are configured to alternately engage opposite sides of the flow path when bending the flow path so as to engage and depress a side of the flow path and urge the second portion of the cannula to move along the flow path and separate from the first portion of the flow path.

5. The apparatus of claim 1 in which the first and second stations are located so that when the cannula is received therein, the breakable portion of the frangible cannula is generally axially aligned with or in proximity to a center of an arc of movement.

6. The apparatus of claim 1 in which the one angle is 60 degrees or less and the greater angle is 80 degrees or less.

7. The apparatus of claim 1 in which the second station actuator is configured to repeatedly bend a portion of the cannula in opposite directions.

8. The apparatus of claim 1 including a bag support for suspending a bag therefrom, the bag support being located relative to the first and second stations such that when a bag is suspended on the support, the first and second portions of a frangible cannula within a bag port are located in proximity with the first and second stations in the load position for ease of insertion therein.

9. The apparatus of claim 1 wherein the stationary first station includes a pair of spaced apart members for receiving the flow path and first portion of the cannula therebetween, the spaced apart members being configured with interfering surfaces to help retain the flow path and cannula between the members.

10. The apparatus of claim 1 further comprising an optical sensor positioned to detect the presence of a tube defining the flow path in the correct position in the first and second stations for breaking the cannula.

11. The apparatus of claim 1 in which the actuator is configured to pivot the second station consecutively through at least a third angle relative to the initial loading position greater than the second angle and in the opposite direction from the second angle.

12. Apparatus for breaking a frangible cannula located inside a flexible flow path, the frangible cannula including first and second portions with a breakable junction therebetween that may be broken by relative bending of the portions, the apparatus comprising: a housing having a face and carrying a stationary first station in which the portion of the flow path containing the first portion of the cannula is positionable and a pivotable second station in which the portion of the flow path containing the second portion of the cannula is positionable; an actuator for pivoting the second station in opposite directions from an initial loading position in which the first and second stations are generally aligned to bend the flow path and the second portion of the cannula therein relative to the other portion of the flow path and the first portion of the cannula therein to break the breakable junction; the housing including a bag support for suspending a bag having a port tube with a frangible cannula therein, the bag support being positioned such that when a bag is suspended on the support, the port tube and first and second portions of the frangible cannula are respectively located in proximity to the first and second stations in the load position, the stationary first station including a pair of spaced apart members for receiving the port tube and first cannula portion therebetween, each of the spaced apart members including a port tube holder extending radially from the respective member at a location spaced from the face to help retain the port tube between the holders and the face of the housing during bending, wherein the actuator pivots the second station to bend the second portion of the cannula through one angle from the loading position in one direction and through a greater angle from the loading position in the opposite direction.

13. The apparatus of claim 12 in which the second station is configured for movement through an arc relative to a center of rotation.

14. The apparatus of claim 13 in which the second station includes a pair of extending fingers for receiving the flow path and the second portion of the cannula therebetween, and wherein the fingers are off-set relative to the center rotation.

15. The apparatus of claim 13 in which the first and second stations are located so that when the cannula is received therein, the breakable portion of the frangible cannula is generally axially aligned with or in proximity to the center of rotation.

16. The apparatus of claim 12 in which each port tube holder comprises a ring on the spaced apart member.

17. The apparatus of claim 12 in which each port tube holder comprises a resilient ring.

18. The apparatus of claim 12 further comprising an optical sensor positioned to detect the presence of a port tube in the correct position in the first and second stations for breaking the cannula.

19. Apparatus for breaking a frangible cannula located inside a flexible flow path, the frangible cannula including first and second portions with a breakable junction therebetween that may be broken by relative bending of the portions, the apparatus comprising:

a stationary first station in which the portion of the flow path containing the first portion of the cannula is positionable and a pivotable second station in which the portion of the flow path connected to the pivotable containing the second portion of the cannula is positionable;

an actuator connected to the pivotable second station and pivoting the second station about a pivot axis from an initial loading position, in which the first and second stations are generally aligned, through one angle from the initial loading position in one direction and through a greater angle from the initial loading position in an opposite direction, the stationary first station being stationary relative to the initial loading position, wherein the second pivotable station is operable to bend the flow path and second portion of the cannula therein relative to the other portion of the flow path and the first portion of the cannula therein through a first angle in one direction and through a second greater angle in an opposite direction to break the breakable junction;

the actuator including an electrical stepper motor and a drive assembly transmitting rotation of the motor to the second station to pivot the second station, the drive assembly being configured to increase the torque provided by the motor to the second station.

20. The apparatus of claim 19 wherein the motor rotates about an axis that extends at right angle to the pivot axis.

21. The apparatus of claim 20 including a base and wherein the first bevel gear is carried on the base to rotate about an axis that extends at a right angle to the pivot axis and the second bevel gear is carried by the base to rotate about the pivot axis.

22. The apparatus of claim 19 wherein the drive assembly includes first and second bevel gears engaged to transmit rotation of the motor to the second station, the bevel gears being sized to increase torque transmitted from the motor to the second station.

* * * * *